(12) United States Patent
Duval et al.

(10) Patent No.: US 6,620,108 B2
(45) Date of Patent: Sep. 16, 2003

(54) APPARATUS AND METHOD FOR DETERMINING MACHINE OPERATOR STATUS

(76) Inventors: Landon Duval, 1200 Pacific Coast Hwy., #316, Huntington Beach, CA (US) 92648; Ronald Louis Williams, 35569 Rice Canyon Rd., Fallbrook, CA (US) 92028

( * ) Notice: Subject to any disclaimer, the term of this patent is extended or adjusted under 35 U.S.C. 154(b) by 0 days.

(21) Appl. No.: 10/033,636

(22) Filed: Dec. 26, 2001

(65) Prior Publication Data

US 2003/0120139 A1 Jun. 26, 2003

(51) Int. Cl.[7] ............................................... A61B 5/00
(52) U.S. Cl. ........................ 600/532; 73/23.3; 422/84; 340/573.1
(58) Field of Search .................. 600/532; 73/233; 422/84; 340/573.1

(56) References Cited

U.S. PATENT DOCUMENTS

| | | |
|---|---|---|
| 4,090,078 A | 5/1978 | Heim |
| 4,277,251 A | 7/1981 | Leichnitz |
| 4,363,635 A | 12/1982 | Hutson |
| 4,649,027 A | 3/1987 | Talbot |
| 4,749,553 A | 6/1988 | Lopez et al. |
| 4,849,180 A | 7/1989 | Fukui |
| 4,905,498 A | 3/1990 | O'Donnell et al. |
| 4,926,164 A * | 5/1990 | Porter et al. ............... 340/576 |
| 5,055,268 A | 10/1991 | Martin |
| 5,220,919 A | 6/1993 | Phillips et al. |
| 5,369,977 A * | 12/1994 | Rhodes et al. ............... 73/23.3 |
| 5,376,555 A | 12/1994 | Forrester et al. |
| 5,743,349 A | 4/1998 | Steinberg |
| 6,075,444 A | 6/2000 | Sohege et al. |
| 6,097,480 A | 8/2000 | Kaplan |
| 6,183,418 B1 | 2/2001 | Kuennecke |

* cited by examiner

Primary Examiner—Robert L. Nasser
(74) Attorney, Agent, or Firm—Gene Scott-Patent Law & Venture Group

(57) ABSTRACT

An apparatus and method for assuring that a machine operator is not under the influence of a chemical, comprising a first sensor positioned proximally to the machine operator and adapted for, measuring a vapor concentration proximal thereto, a second sensor positioned distally from the machine operator and adapted for measuring the vapor concentration distally from the operator, a device for comparing the proximal and distal vapor concentrations, and an automated remediating device responsive to the comparing device when the ratio of the first and the second vapor concentrations are within a specified range.

12 Claims, 2 Drawing Sheets

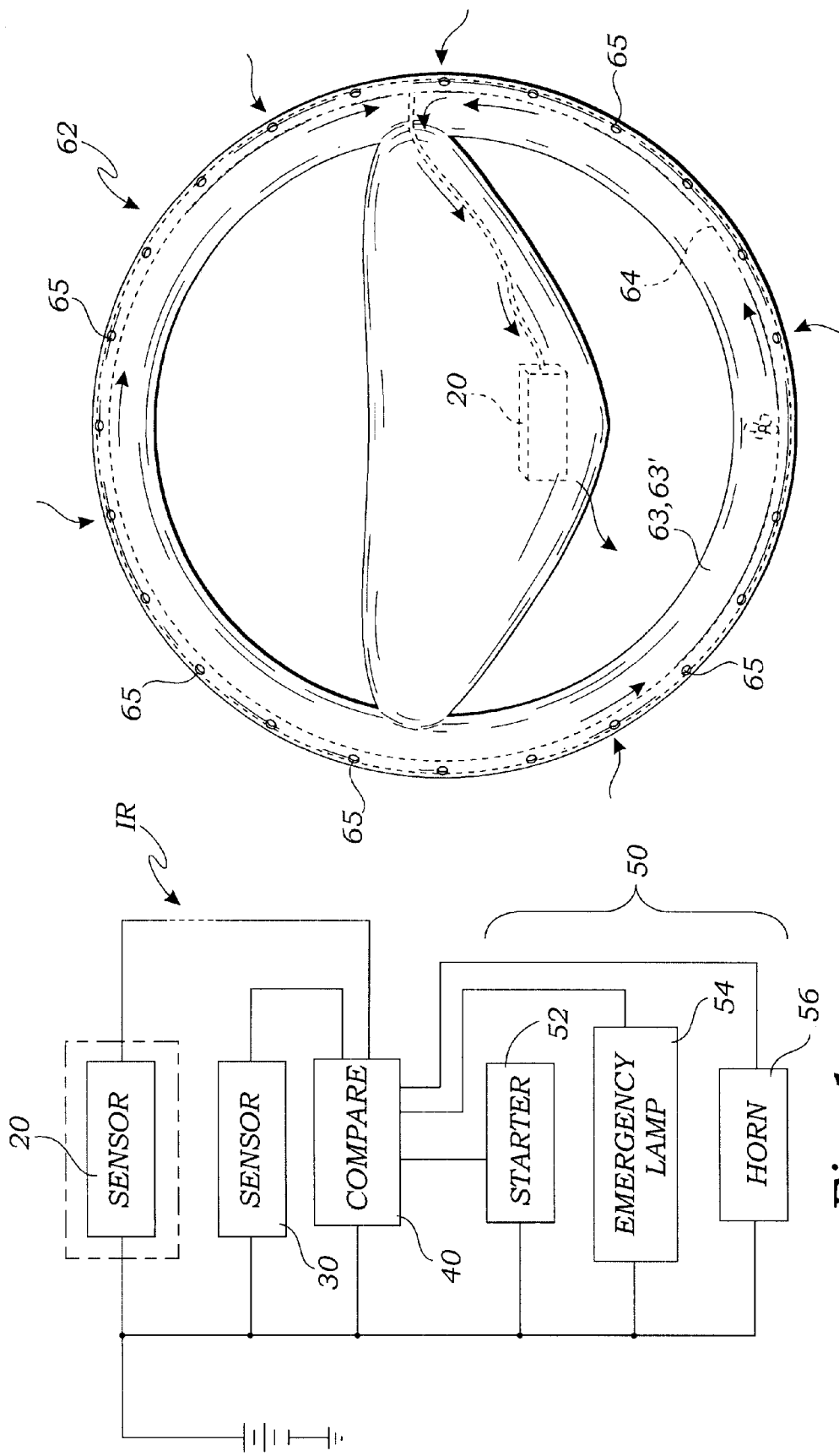

APPARATUS AND METHOD FOR DETERMINING MACHINE OPERATOR STATUS

BACKGROUND OF THE INVENTION

1. Field of the Invention

This invention relates generally to apparatus and methods for determination of alcohol consumption in machinery operation, and in particular to a comparison technique for determination of the status of a machine operator with respect to a chemical.

2. Description of Related Art

The following art defines the present state of this field:

Heim, U.S. Pat. No. 4,090,078 describes a method for determining the alcohol content in the exhaling respiratory air using an alcohol measuring instrument and measuring the alcohol content when the exhaling air transmits the determined value of the alcohol concentration. This determined value of alcohol concentration occurs when the time variation related to the height of the alcohol signal is below a predetermined threshold value and the velocity of flow of the exhaling air is above a given value and is maintained without interruption for a given time. The apparatus includes an infrared measuring instrument which is connected into the respiratory air current and measures the alcohol concentration of the exhaling air. This value is applied to an indicator through a linear gate when an AND-gate is triggered by threshold comparators and a timing element activated by a threshold comparator.

Leichnitz, U.S. Pat. No. 4,277,251 describes a method of determining the alcohol content of air exhaled by a person using a flow through testing tube having an alcohol indicating material therein and a sampling tube to which the air is directed which has a material therein for retaining the alcohol of the breathing air and also using a suction pump comprises cooling the sampling tube, passing the exhaled air through the cooled sampling tube, measuring a volume of the air passing through the cooled sampling tube, heating the sampling tube and connecting the suction pump to the sampling tube to suck flushing air through the heated tube and then through the testing tube. The sampling tube advantageously contains a silica gel to retain the alcohol therein. The volume measuring device may be a measuring bag.

Hutson, U.S. Pat. No. 4,363,635 describes a method and apparatus for discriminating between alcohol and acetone in a breath sample and accurately measuring the alcohol level when acetone is present in the sample. The breath sample is measured with two different types of detectors and their outputs compared. One detector uses the principles of infrared (IR) absorption, the other detector is a semiconductor, commonly called a Taguci cell, or its equivalent. Automatic correction is provided for variation in sensitivity of the semiconductor.

Talbot, U.S. Pat. No. 4,649,027 describes a battery-operated portable breath tester. The breath tester includes a housing which defines a sleeve for receiving a wand. The wand defines an internal sample chamber, with a lamp at one end for providing infrared energy and a detector at an opposite end for receiving the infrared energy after it has passed through the sample to be tested. The wand defines opening extending from the internal sample chamber to the outside of the wand. The wand has an external shape providing a snug fit within the sleeve. As the wand is moved within the sleeve, gas is purged from the wand. The wand is connected to the housing by means of an electrical coil. The housing encloses a digital voltmeter including a digital display for providing a test readout. The digital voltmeter includes an oscillator which is coupled through a frequency divider and a transistor switch to the lamp. The lamp is switched on and off in accordance with the frequency output of the frequency divider to modulate the infrared energy emitted from the lamp at a selected frequency. A voltage regulator is connected to the lamp, and the lamp and voltage regulator are located in heat-exchange relationship with the sample chamber. This aids in raising the temperature of the sample chamber during testing in order to alleviate condensation.

Lopez, U.S. Pat. No. 4,749,553 describes a breath alcohol detector measuring and compensating for distance between the mouth of the individual exhaling breath into the ambient air and the detector, the atmospheric pressure, and the temperature. Blood alcohol content information is calculated using these compensation factors and a signal obtained from an electrochemical fuel cell which is indicative of the amount of alcohol or other gas contained in the sample. The detector also includes a reciprocally acting electromagnetically energized motor which drives a diaphragm pump to draw the sample into the electrochemical fuel cell.

Fukui, U.S. Pat. No. 4,849,180 describes an alcohol selective gas sensor including a detecting electrode and a semiconductor detecting element in contact with the detecting electrode, the semiconductor detecting element comprising tin oxide ($SnO_2$) and a metal oxide of at least one of alkaline earth metals (Be, Mg, Ca, Sr, Ba) carried by the tin oxide, the metal oxide being contained in an amount of about 0.5 mol % or above.

O'Donnell et al., U.S. Pat. No. 4,905,498 describes a gaseous detection system for detecting the existence of a certain gas and further the detection of a certain level or percentage of that certain gas within a certain environment. An example is use of the gas detection system in a motor vehicle to aid in determining when a driver of the motor vehicle may be driving under the influence of alcohol, and for providing an appropriate warning signal that may be viewed from the exterior of the motor vehicle. The system includes a sensor unit for sensing ethanol in the atmospheric contents of the motor vehicle's interior, for example, a unit for providing an actuation signal in response to the sensing unit, and a signal unit that generates a signal which can be utilized for many purposes, for example, causing at least some of the exterior lights on the motor vehicle to alternately flash on and off in a substantially non-standard pattern. The sensing unit may also be coupled with a digital readout device or the like to indicate the amount of blood alcohol content of a person for evidentiary or like purposes.

Martin, U.S. Pat. No. 5,055,268 describes an air-borne chemical sensor system including a motor and impeller to draw an air sample into a housing containing a sensor which will provide a signal for display related to the amount of a particular air-borne chemical in a given air sample. The system is controllable by different duration activation of a single activating switch which can further control a secondary function, such as a flashlight.

Phillips, U.S. Pat. No. 5,220,919 describes a gaseous detection system for detecting the existence of a certain gas and further the detection of a certain level or percentage of that certain gas within a certain environment. An example is use of the gas detection system in a motor vehicle to aid in determining when a driver of the motor vehicle may be driving under the influence of alcohol, and for providing an appropriate warning signal that may be viewed from the exterior of the motor vehicle. The system includes a sensor unit for sensing ethanol in the atmospheric contents of the motor vehicle's interior, for example, a unit for providing an actuation signal in response to the sensing unit, and a signal unit that generates a signal which can be utilized for many purposes, for example, causing at least some of the exterior lights on the motor vehicle to alternately flash on and off in a substantially non-standard pattern. The sensing unit may also be coupled with a digital read-out device or the like to indicate the amount of blood alcohol content of a person for evidentiary or like purposes.

Forrester et al., U.S. Pat. No. 5,376,555 describes a method and infrared sensing device for determining the concentration of alveolar alcohol in a breath sample exhaled by a subject into an infrared sensing device. The presence of alcohol from the upper respiratory tract of the subject is detected by continuously monitoring alcohol and carbon dioxide, normalizing alcohol values with respect to carbon dioxide, calculating a difference between normalized alcohol concentration and carbon dioxide concentration over time, integrating (summing) the difference, and comparing the integrated difference with a threshold. This technique accurately and consistently detects the presence of mouth alcohol in the sample before the presence of carbon dioxide which originates in deep lung breath.

Steinberg, U.S. Pat. No. 5,743,349 describes a vehicle ignition interlock system including a non-invasive reader of a person's blood-alcohol concentration in combination with ignition interlock circuitry that prevents operation of a vehicle by an intoxicated person. The non-invasive blood-alcohol concentration reader, termed alcoh-meter, utilizes optical spectroscopic electromagnetic radiation technology to determine the alcohol levels in the blood. The alcoh-meter is preferably a dash mounted sensor for receiving a person's finger and absorbing incident light from a multiple wavelength light source and causing a light absorption reading to be generated based on the person's blood alcohol concentration in the finger tissue. After registering a reading, the results are compared electronically against a table of impaired/non-impaired levels of blood alcohol concentration. The impaired/non-impaired results are communicated to interlock circuitry that either enables, or disables startup of the vehicle. If an impaired status is determined, the results are displayed instructing the operator to wait, or find a non-impaired operator.

Soheege et al., U.S. Pat. No. 6,075,444 describes an arrangement for blocking the operation by an intoxicated operator of a machine or a motor vehicle. The arrangement has a measuring apparatus which determines the blood alcohol content of the operator and an evaluation unit connected to the machine or motor vehicle. The evaluation unit receives measurement data supplied by the measurement apparatus and enables the machine or motor vehicle when the measurement data satisfies at least one predetermined condition. The arrangement is improved in that the sobriety of the operator is recognized before the starting operation of the machine or motor vehicle without it being necessary to supply a breath sample. The measuring apparatus includes a gas sensor which is a sensor for measuring the blood alcohol content via permeation through the skin of the operator. The measuring apparatus is configured so that it can be worn by the operator preferably on the leg or arm.

Kaplan, U.S. Pat. No. 6,097,480 describes a vehicle interlock system which utilizes non-invasive, optically based methods for detecting and measuring levels of certain target chemical substances in the blood or tissues of a user in preventing operation of the vehicle by persons exhibiting higher (or lower) than prescribed levels of such chemicals. The system of the present invention is not limited to simply measuring blood alcohol levels as are presently available breathalizer-based interlock systems, but lends itself to use in detecting unacceptable systemic levels of virtually any chemical for which the system if programmed to measure. In addition, the present system includes components for positively identifying, and during the course of vehicle operation, re-identifying the intended user and alcohol or drug user testee.

Kuennecke; U.S. Pat. No. 6,183,418 describes the process for detection and for quantitative determination of substances emitted or perspired through the skin is derived from flow diffusion analysis. The measuring system conceived for this purpose uses a diffusion half cell through which an acceptor medium flows and which is closed by a membrane. For the duration of the measurement, the membrane is brought into contact with the skin or a closed gas volume formed over the skin. With the process and the related measuring system, the blood alcohol level can be determined with a good degree of precision indirectly via the quantity of (gaseous) ethanol emitted through the skin.

The prior art teaches the use of alcohol and other substance sensing devices used for determining the condition of a machine operator, but fails to teach a device and comparison method and the use of the steering wheel for collection of samples. The present invention fulfills these needs and provides further related advantages as described in the following summary.

SUMMARY OF THE INVENTION

The present invention teaches certain benefits in construction and use which give rise to the objectives described below.

An apparatus and method for determining machine operator status comprises a first sensor positioned proximally to the machine operator and adapted for measuring a vapor concentration proximal thereto, a second sensor positioned distally from the machine operator and adapted for measuring the vapor concentration distally from the operator, a device for comparing the proximal and distal vapor concentrations, and an automated remediating device responsive to the comparing device when the ratio of the first and the second vapor concentrations are within a specified range.

A primary objective of the present invention is to provide an apparatus and method of use of such apparatus that provides advantages not taught by the prior art.

Another objective is to provide such an invention capable of alerting a machine operator and those near the machine that the operator is potentially influenced by a chemical such as alcohol.

A further objective is to provide such an invention capable of shutting down the machine when a chemical level differential is detected.

A still further objective is to provide such an invention easily mounted onto the steering wheel of a vehicle.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention. In such drawings:

FIG. 1 is a block diagram of the invention showing signal paths;

FIG. 2 is an elevational view of a steering wheel sample collection device thereof.

DETAILED DESCRIPTION OF THE INVENTION

Figure 3:
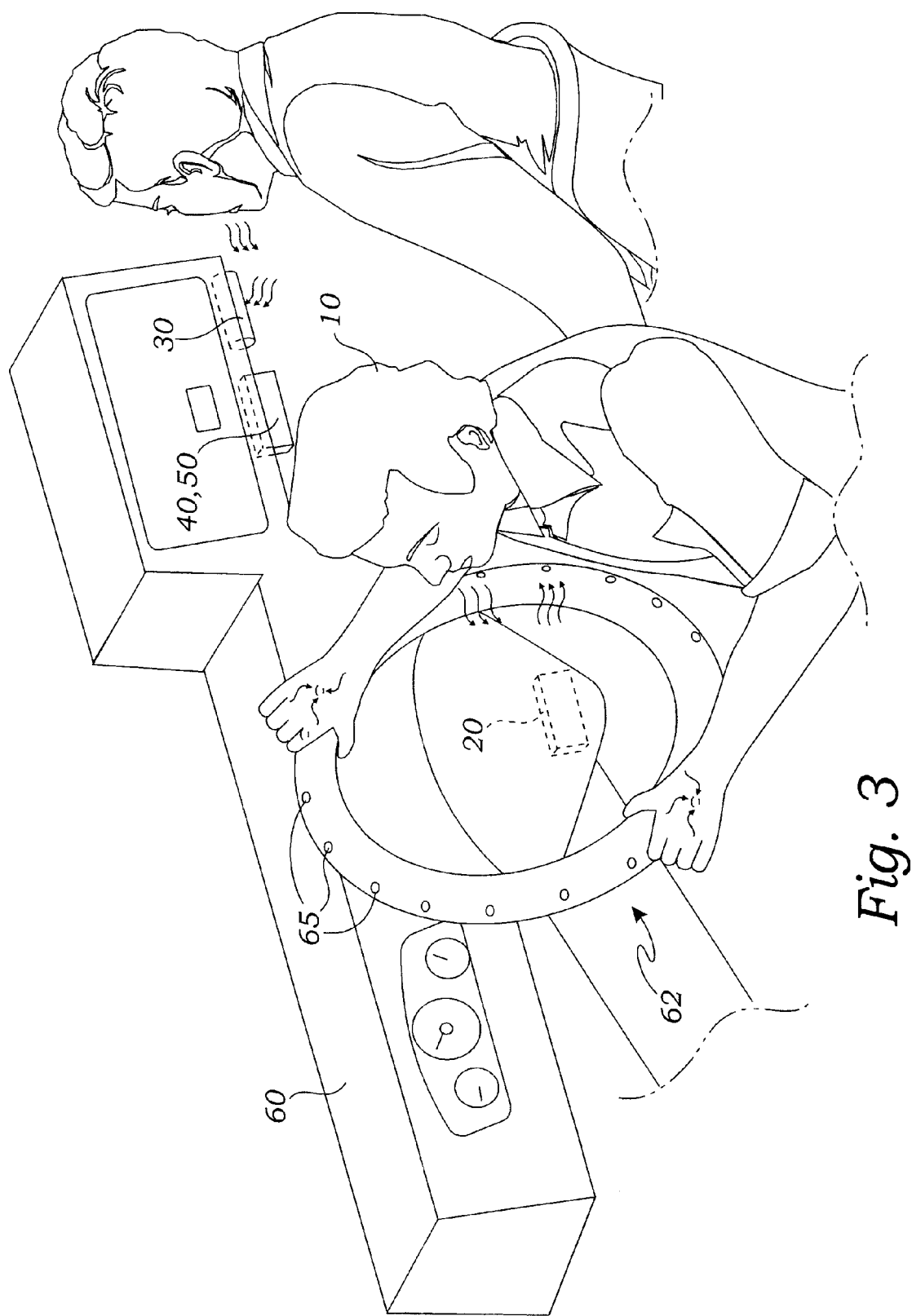
FIG. 3 is a perspective view thereof showing the interior of a machine cab and placement of the elements of the invention.

The above-described drawing figures illustrate the invention in at least one of its preferred embodiments, which is further defined in detail in the following description.

The present invention is an apparatus and method for assuring that a machine operator 10 is not under the influence of a chemical such as alcohol. A first sensor or detector 20 is positioned proximal to the machine operator 10 and is adapted for measuring a first concentration level of the chemical. A second sensor 30 is positioned distal to the machine operator 10 and is adapted for measuring a second concentration level of the chemical. A means for comparing 40 of the proximal and distal vapor concentration levels provides a signal to an automated remediation means 50 responsive to the comparing means for enabling a remedial action. In FIG. 1, the remediation means 50 may be any or all of the three items identified by reference numerals 52, 54, and 56. Such remedial means may comprise solenoid or other types of actuators and servomechanisms of various types well known in the art for automatically enabling or disenabling machine functions. Preferably, the first and the second sensors 20, 30 are adapted for measuring a concentration of alcohol vapor in air by an infrared spectroscopy method. This type of sensor is well described in the prior art, such as U.S. Pat. No. 4,090,078, U.S. Pat. No. 4,363,635 and U.S. Pat. No. 4,649,027 which are hereby incorporated into this application by reference to teach the use of the infrared spectral techniques adapted for identification of one or more specific spectral lines as an indicator of the presence of a substance in a gas or vapor stream. In the preferred embodiment, the first and the second sensors 20, 30, the comparing means 40 and the remediation means 50 are adapted for mounting within a machine 60 such as an automobile or truck.

Preferably, the first of the sensors 20 is positioned on or inside the structure of a steering wheel 62 of the machine 60 and the second of the sensors 30 is positioned distally therefrom, typically in a lateral direction from the first sensor 20 as shown in FIG. 3. In this embodiment, the steering wheel 62, or preferably, a steering wheel cover 63, provides a collection space 64, preferably a tube or series of tubes, and a means for admittance 66 of the alcohol vapor into the collection space 64 in proximity to the first of the sensors 20. Thus vapors may be collected and spectrally analyzed for, for instance, the spectral lines specific to the substance ethanol, which is found in quantity in most alcoholic beverages. The first sensor 20 may alternately provide a means for sensing alcohol at, or on, the skin of the operator. The contact sensor 63', which may be made a part of the exterior surface of the cover 63, and its method of use is described in U.S. Pat. No. 6,075,444 and in U.S. Pat. No. 5,220,919 which are hereby incorporated into this application by reference. Sensor 20 preferably provides a suction device to draw a mixture of vapor and air from the cabin of the vehicle into the sensor 20 for analysis. Small arrows are shown in FIG. 2 to depict the drawing in of air in the vicinity of the steering wheel 62 through small apertures 65 and the path of such air leading to the sensor 20.

The comparing means 40 is preferably an operational amplifier circuit or AND or OR gates may be used. This is well known in the art.

The remediation means 50 is enabled for, at least one of: disabling the machine, visually signaling, audibly signaling and event recording. For instance, in an automobile application, where it is desired to prevent a driver with alcohol in his/her system from starting or from operating the vehicle, the remediation action may be to disable the vehicle's starter.or ignition system. Alternately, the remediation action may be to set the vehicle's horn or lights into action to alert the driver and others. In some instances, the remediation action may be to simply record the incident for supervisory notification. Elements 52, 54 and 56 shown in FIG. 1, are the mechanisms and devices that may be used to effect the respective portions of the corresponding automotive systems. In FIG. 1, power conductors are shown at the left side of the diagram, while control signals are shown at the right side. It should be noticed that the first sensor 20 may be enable for infrared (IR) signaling to comparing means 40 so that no hard wiring is required between the steering wheel 62 and the comparing means 40 and the remediation means 50 which are not typically mounted on the steering column. In FIG. 3, the elements 40 and 50 are shown incorporated into a single package.

The method of operating the system reflects the above physical description. It includes positioning the first sensor proximal to a machine operator, such as the driver of an automobile, and adapting the first sensor for measuring a first level of a chemical concentration that may be included in the ambient environment within the vehicle. Of course this, adaptation includes the calibration of the sensor to the specific substance of interests. Further, the method includes positioning the second sensor distal to the machine operator and adapting the second sensor, in a similar manner, for measuring a second level of the chemical concentration. The second sensor may be located as shown in FIG. 3, or elsewhere within the vehicle. Both sensors may operate under the same principle, or they may operate under different principles. Signals are generated by the sensors (detectors) and are conducted to the comparing means so as to compare the proximal and distal vapor concentration levels. This comparison is used to determine if a remedial action is necessary. For instance, if the first sensor signal is significantly stronger than the second sensor signal, the comparator initiates an action signal capable of shutting-down the starter of the vehicle or implementing other actions such as activation of the vehicle's horn or emergency lamps, etc. Alternately, the action may be to only record the occurrence. Clearly, other actions may be taken and all such actions are easily implemented by those of skill in the art. U.S. Pat. No. 5,743,349 and U.S. Pat. No. 4,905,498 are hereby incorporated into this application by reference so as to teach sensor mounting and use methods and a few of the methods of the actions that may be taken when necessary, i.e., disabling the starter of a vehicle.

The method, as described or inferred above, includes some or all of the steps of: adapting the first and the second sensors for measuring a concentration of alcohol vapor in air, enabling the sensors for an infrared spectroscopy method, for example, establishing a comparing means and a remediation means adapted for mounting within a machine, such as a vehicle, positioning the first of the sensors on a steering wheel of the machine and the second of the sensors distally therefrom, providing a collection space and a means for admittance of the alcohol vapor into the collection space in proximity to the first of the sensors, enabling the first sensor for sensing alcohol at the skin of the operator in a contact measurement, and any one or more of the steps of disabling the machine, visually signaling, audibly signaling and event recording upon receipt of a command.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. An apparatus for assuring a machine operator in a machine is not under the influence of a chemical, the apparatus comprising: a first sensor positioned on a steering wheel of the machine, proximal to the machine operator; the first sensor enabled for measuring a first level of a chemical concentration; the steering wheel providing a collection space and a means for admittance of the chemical concentration into the collection space in proximity to the first sensor; a second sensor positioned distal to the machine operator and adapted for measuring a second level of the chemical concentration; a means for comparing the proximal and distal vapor concentration levels; and an automated remediation means responsive to the comparing means for enabling a remedial action.

2. The apparatus of claim 1 wherein the first and the second sensors are adapted for measuring a concentration of alcohol vapor in air.

3. The apparatus of claim 2 wherein the alcohol vapor sensors are enabled for an infrared spectroscopy method.

4. The apparatus of claim 1 wherein the first and the second sensors, the comparing means and the remediation means are adapted for mounting within a machine.

5. The apparatus of claim 1 wherein the first sensor provides a means for sensing alcohol at the skin of the operator.

6. The apparatus of claim 1 wherein the remediating means is enabled for, at least one of: disabling the machine, visually signaling, audibly signaling and event recording.

7. A method for assuring that a machine operator is not under the influence of a chemical, the method comprising: positioning a first sensor proximal to a machine operator, the first sensor mounted on a steering wheel of a machine; adapting the first sensor for measuring a first level of a chemical concentration; providing a collection space and a means for admittance of the chemical concentration into the collection space in proximity to the first sensor; positioning a second sensor distal to the machine operator and adapting the second sensor for measuring a second level of the chemical concentration; comparing the proximal and distal vapor concentration levels; and acting remedially in response to the comparing means.

8. The method of claim 7 further comprising the step of adapting the first and the second sensors for measuring a concentration of alcohol vapor in air.

9. The method of claim 8 further comprising the step of enabling the alcohol vapor sensors for an infrared spectroscopy method.

10. The method of claim 7 further comprising the step of the first and the second sensors, the comparing means and the remediation means are adapted for mounting within a machine.

11. The method of claim 7 further comprising the step of enabling the first sensor for sensing alcohol at the skin of the operator in a contact measurement.

12. The method of claim 7 further comprising the step of at least one of: disabling the machine, visually signaling, audibly signaling and event recording upon command.

\* \* \* \* \*